US006229060B1

United States Patent
Vidal et al.

(10) Patent No.: US 6,229,060 B1
(45) Date of Patent: May 8, 2001

(54) METHOD OF METATHESIS OF ALKANES AND CATALYST

(75) Inventors: Véronique Vidal, Villeurbanne; Albert Theolier, Decines; Jean Thivolle-Cazat, Fontaines sur Saone; Jean-Marie Basset, Villeurbanne, all of (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 09/147,507

(22) PCT Filed: Jul. 10, 1997

(86) PCT No.: PCT/FR97/01266

§ 371 Date: Mar. 12, 1999

§ 102(e) Date: Mar. 12, 1999

(87) PCT Pub. No.: WO98/02244

PCT Pub. Date: Jan. 22, 1998

(30) Foreign Application Priority Data

Jul. 12, 1996 (FR) .................................................. 96 09033

(51) Int. Cl.$^7$ ....................................................... C07C 6/08
(52) U.S. Cl. ............................................................. 585/708
(58) Field of Search ............................................... 585/708

(56) References Cited

U.S. PATENT DOCUMENTS 4,467,047   8/1984   Johnson ................................ 502/246

FOREIGN PATENT DOCUMENTS 0 076 371 A1   8/1982   (EP) .
WO 90/14323   11/1990   (WO) .

*Primary Examiner*—Walter D. Griffin
*Assistant Examiner*—Thuan D. Dang
(74) *Attorney, Agent, or Firm*—Jacobson, Price, Holman & Stern, PLLC

(57) ABSTRACT

A process for the metathesis of linear or branched starting alkanes involves, first, grafting metal atoms in the form of hydrides to a solid oxide, such that the grafted metal atoms are dispersed over the solid oxide, which effects a solid catalyst, and second, reacting the starting alkanes over the solid catalyst.

34 Claims, No Drawings

METHOD OF METATHESIS OF ALKANES AND CATALYST

The present invention relates to a process for the metathesis of alkanes.

It is well known that alkanes commonly known as paraffins are molecules which are difficult to convert because of their chemical inertia.

It is known to convert alkanes by hydrogenolysis reactions of carbon—carbon bonds. It has been possible, over certain metal catalysts, simultaneously to observe homologation reactions of alkanes but the latter always remain very minor reactions with respect to the hydrogenolysis reactions. This is because these reactions are always carried out in the presence of hydrogen, at temperatures varying from 250 to 350° C., in contact with catalysts based on transition metals in massive form or in the form of films or else in the form of metal particles supported on oxides. The best results seem to have been obtained by Donohoe, Clarke and Rooney with linear $C_5$ to $C_7$ alkanes over tungsten film (J. Chem. Soc. Farad. Trans. I, 1980, 76, 345; J. Chem. Soc. Chem. Commun., 1979, 648); the reaction proves to be slower by an order of magnitude with branched alkanes and does not take place with cyclic alkanes. Sarkany has also studied the homologation of butane and various $C_4$ or $C_5$ alkanes over catalysts of nickel black, $Ni/SiO_2$, platinum black, $Pt/SiO_2$ or $Pd/Al_2O_3$ type (J. Chem. Soc. Farad. Trans. I, 1986, 82, 103; J. Catal., 1984, 89, 14); this reaction is also favoured in the case of linear alkanes with respect to branched alkanes but always remains a minor process beside isomerization reactions (for example of butane to isobutane over $Pt/SiO_2$) or hydrogenolysis reactions (over $Ni/SiO_2$). The homologation-aromatization of pentane or cyclopentane to benzene has been reported by Peter and Clarke over rhodium film alloyed with copper, tin, gold or silver (J. Chem. Soc. Farad. Trans. I, 1976, 72, 1201) and by Sarkany over $Ni/SiO_2$ (J. Chem. Soc. Chem. Commun., 1980, 525); only alloyed rhodium films give a suitable selectivity for benzene while hydrogenolysis remains predominant with nickel catalysts, even for reduced conversions. Thus, the performances of these known homologation reactions of alkanes remain very modest or linked to an aromatization process.

Nevertheless, if it were known how to convert alkanes into their higher homologues, this would constitute a means for enhancing the value of certain petroleum fractions, such as in particular the $C_4$ or $C_5$ fractions. It would be possible to envisage numerous applications in the field of oils, fuels, polymers or organic chemical synthesis, making it possible to lengthen side chains or to obtain higher branched hydrocarbons by other routes than acidic or superacidic catalysis. This is because it is known that high octane numbers are particularly desired in the field of fuels. It is also well known that low molecular weight alkanes cannot be enhanced in value to any significant extent, whereas heavier alkanes are of greater commercial interest.

The object of the present invention is thus to provide a process which makes it possible to convert alkanes into their higher and lower homologues with high selectivity.

Another object of the invention is to provide such a process which has a wide field of application which can cover, simultaneously, the fields of oils, fuels, polymers or organic chemical synthesis, the elongation of the side chains of compounds comprising them or the production of higher branched hydrocarbons. Such an object is thus in particular the enhancement in value of light alkanes to heavier alkanes of greater advantage industrially.

Another object of the invention is to provide such a process which can be employed under moderate operating conditions, namely in particular at relatively low temperature and relatively low pressure.

Yet another object of the invention is to provide novel catalysts of use in the context of the process for the metathesis of alkanes.

It has been discovered, which is the subject-matter of the present invention, that it is possible, by using the catalysts of the invention, to carry out the metathesis of alkanes to higher and lower homologues with high selectivity and even at low temperature, in particular at temperatures of less than 200° C.

A subject-matter of the invention is therefore a process for the metathesis of linear or branched starting alkanes, in which process the starting alkane or alkanes is/are reacted over a solid catalyst comprising a metal hydride grafted to and dispersed over a solid oxide. It seems probable that this catalyst acts as catalytic precursor. When it is brought into the presence of alkanes, this catalyst has a tendency to form an alkylmetal complex which would be the catalytically active species.

The reaction according to the invention provides for the metathesis of sigma C—C bonds and the conversion of an alkane into its higher and lower homologues. Thus, starting with an alkane, for example ethane, it is possible to obtain, directly and successively, all the higher alkanes and in particular branched alkanes.

The reaction can be written according to the equation:

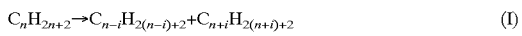

$$C_nH_{2n+2} \rightarrow C_{n-i}H_{2(n-i)+2} + C_{n+i}H_{2(n+i)+2} \quad (I)$$

i=1, 2, 3 . . . n−1

The invention thus makes possible the direct conversion of light alkanes into heavier alkanes and thus an enhancement in value of these light alkanes, in particular $C_4$–$C_5$ petroleum fractions. It also makes possible the elongation of side hydrocarbon-comprising chains on certain cyclic compounds.

In an entirely preferred way, the catalysts according to the invention are obtained from an organometallic complex of following formula (II):

$$MR_a \quad (II)$$

where

M is a transition metal selected from those of groups 5 and 6 of the Periodic Classification of the Elements, preferably from tantalum, tungsten and chromium;

the R groups are identical or different, saturated or unsaturated, preferably $C_1$ to $C_{10}$, hydrocarbon-comprising ligands bonded to the M by one or more carbons (it being possible for the metal-carbon bonds to be simple, double or triple bonds);

a is less than or equal to the valency of M, which is 5 or 6.

Mention may in particular be made, among the appropriate ligands, of methyl, neopentyl, neopentylidene, neopentylidyne, benzyl or their mixtures, for example neopentyl-neopentylidene or neopentyl-neopentylidine.

The neopentyl-neopentylidene and neopentyl-neopentylidine mixtures are particularly advantageous when complexed with tantalum, respectively tungsten.

According to an embodiment which is particularly appropriate to the use of the solid catalyst, the dispersing and the grafting of the organometallic compound are carried out over and to a very anhydrous solid oxide. The solid oxide, for example silica, is subjected to an exhaustive heat treatment (with the intention of providing for dehydration and dehydroxylation), in particular between 200 and 1100° C. for several hours (for example, from 10 to 20 hours). Of course, a person skilled in the art will take care not to exceed the degradation temperature or stability limit temperature of the solid oxide which he has chosen to use. For silica, the dehydration is carried out between 200 and 500° C., preferably in the vicinity of 500° C., for a simple dehydration reaction or at a temperature greater than 500° C., if it is desired additionally to obtain the formation of surface siloxane bridges.

The transfer of the complex onto the solid oxide can be carried out in particular by sublimation or in solution.

In the case of sublimation, the organometallic complex in the solid state is heated under vacuum and under temperature conditions which provide for its sublimation and its migration in the vapour state onto the solid oxide, which itself is preferably in the pulverulent state or in the form of pellets or the like. The sublimation is carried out in particular between 50 and 150° C., preferably in the vicinity of 80° C. The deposition can be monitored, for example by infrared spectroscopy.

The grafting takes place by reaction of the complex with the functional groups of the support (OH, Si—O—Si, and the like). The grafting will preferably be carried out at a temperature greater than or equal to ambient temperature.

It may be desirable to remove the excess complex which has not reacted and which has been simply adsorbed at the surface of the oxide by a reverse sublimation.

A treatment under hydrogen or in the presence of another appropriate reducing agent is subsequently carried out under conditions resulting in the conversion of the metal atoms to hydrides by hydrogenolysis of the hydrocarbon-comprising ligands. It is possible in particular to operate under a pressure of between $10^{-2}$ and 100 bar but preferably at atmospheric pressure. As regards the temperature, it is possible to operate between 25 and 400°C., more generally in the vicinity of 150° C. The reaction is carried out for a sufficient period of time which can range, for example, from 1 h to 24 h, in particular from 10 to 20 h, in particular approximately 15 h.

In the general method which has just been described, it is possible to replace the sublimation by a reaction in solution. In this case, the organometallic complex is in solution in a conventional organic solvent, such as benzene, toluene, pentane or ether, the condition being to be in a very anhydrous medium. The reaction is carried out by suspending solid oxide, preferably pulverulent oxide, in this metal complex solution or alternatively by any other method which provides for appropriate contact between the two media. The reaction can be carried out at ambient temperature and more generally between 25 and 150° C.

The catalysts according to the invention exhibit the following notable characteristics:
- very good dispersion of the metal over the solid oxide, this dispersion being largely, predominantly or completely monoatomic as regards the metal;
- the bonding between the metal atom and the, oxygen of the solid oxide is very strong and makes it possible to maintain the state of dispersion achieved;
- the metal attached to the support is in an advanced state of unsaturation; its d electron shell is highly deficient in electrons (less than 16 electrons); in the cases observed, approximately 10 electrons are present.

Other precursor complexes can be used insofar as they result in a true hydride by the method described or by any other synthetic route.

The metal complexes according to the invention are supported on or grafted to and dispersed over a solid oxide; mention may preferably be made, among the supports of oxide type, of silica, alumina, silicas-aluminas or niobium oxide, zeolites, without the list being limiting.

Among these catalysts, tantalum, tungsten or chromium hydrides grafted to silica or silica-alumina are more particularly recommended.

A subject-matter of the invention is therefore the use of these metal complexes, dispersed over and grafted to solid oxide, in the manufacture of a catalyst for the metathesis of alkanes.

Linear alkanes suitable for the implementation of the process according to the invention can be selected from alkanes comprising at least two carbon atoms; it being possible for the process to be applied to alkanes up to $C_{30}$ and beyond; preferred examples of alkanes are ethane, propane, butane, pentane, and the like.

The process can also be applied to branched alkanes comprising four carbon atoms or more, in particular up to $C_{30}$; preferred examples are: isobutane, isopentane, 2-methylpentane, 3-methylpentane, 2,3-dimethylbutane, and the like.

The process can also be applied to cyclic hydrocarbons (compounds with one or more rings), for example aromatic rings or saturated rings, substituted by at least one linear or branched alkane chain. Mention may be made, by way of example, of cyclic hydrocarbons substituted with at least one linear or branched alkane chain according to the general formula (III):

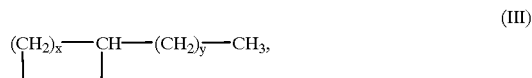

(III)

where:
x is greater than or equal to 2, preferably between 2 and 20;
y is greater than or equal to 0, preferably between 0 and 29.
In these cases, the reaction affects the alkane chains.

The hydrocarbons according to the invention, that is to say saturated linear, branched and/or substituted cyclic (in this case, the reaction taking place on the substitution alkanes) hydrocarbons, can be subjected to the reaction for the metathesis of sigma carbon—carbon bonds with themselves or in the presence of another hydrocarbon.

The process can also be applied to similar compounds comprising one or more heteroatoms, such as O, S or N.

A first method for the application of the process according to the invention consists in reacting the linear, branched or substituted cyclic hydrocarbon by a metathesis reaction with itself, in order to obtain higher and lower homologous alkanes.

A second method consists in reacting with each other at least two hydrocarbons selected from linear, branched and substituted cyclic, so as to obtain branched or substituted cyclic hydrocarbons resulting from reactions for the metathesis of sigma carbon—carbon bonds. More simply, the metathesis reaction is carried out on a mixture of at least two different hydrocarbons.

The reaction for the metathesis of linear, branched or substituted cyclic alkanes is preferably carried out by passing the alkane in the gas phase over the solid catalyst; the gas-phase reaction can be carried out at atmospheric pressure or above, but at a pressure less than or equal to the condensation pressure of the isolated alkane or of the heaviest alkane when there are several starting alkanes. The reaction can also be carried out in the liquid phase in the alkane or in a mixture of alkanes with the catalyst in suspension. The reaction can also be carried out in the presence of an inert gas, such as, preferably, nitrogen, helium or argon.

The metathesis reaction according to the invention can be carried out in a batch reactor, that is to say with a fixed amount of reactants introduced for a complete reaction cycle, in a recycling reactor, in which the alkanes obtained can in particular be recycled, or in a continuous reactor, that is to say with passage of the liquid or gaseous reactant flows over a catalyst bed.

The metathesis reaction can be carried out at temperatures varying from 25 to 300° C. but preferably between 100 and 200° C. The pressure can be between $10^{-2}$ and 100 bar. It is preferable to operate starting from atmospheric pressure.

The reaction for the metathesis of a given alkane results in the formation of its higher and lower alkanes, as shown in the equation (I), with a high selectivity for higher alkane, the attractive compound.

The advantage being in particular in forming higher alkanes, it is possible to provide for recycling the alkanes obtained during the reaction. It can relate both to the recycling of the lower alkane and to the recycling of the higher alkane obtained, in order to continue the reaction towards the production of ever higher alkanes.

It is optionally possible to provide for the separation between higher alkanes and lower alkanes, for example with the intention of recycling the lower alkane or the higher alkane. It is, of course, also possible to recycle the combination, the reaction according to the invention advantageously taking place preferentially on the lower alkanes.

The metathesis reaction according to the invention finds numerous applications in the fields defined above. One of the main applications relates to the production of a high octane number for fuels, in order to improve the stability towards compression. The process according to the invention makes it possible to enrich fuels with heavy and/or branched alkanes, which helps to increase the stability towards compression.

The invention will now be described in more detail using non-limiting embodiments.

EXAMPLE 1
Preparation of the Tantalum Hydride Catalyst:

The $[Ta]_s$—H surface tantalum hydride catalyst can be prepared in the following way: tris(neopentyl) neopentylidenetantalum $Ta[-CH_2-CMe_3]_3-[=CH-CMe_3]$ is sublimed at 80° C. in a glass reactor over silica dehydroxylated beforehand at 500° C., so as to graft the tantalum complex by a reaction at 25° C. with one or more hydroxyl groups of the silica surface, which reaction also produces neopentane:

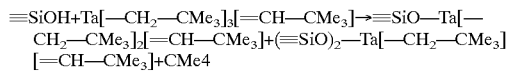

The mixture of neopentyl-neopentylidene complexes obtained:

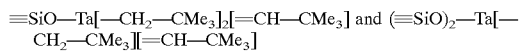

is subsequently treated under hydrogen at atmospheric pressure at 150° C. for 15 h, so as to form the supported tantalum hydride species; this reaction is accompanied by the hydrogenolysis of the neopentyl and neopentylidene ligands, producing methane, ethane, propane, isobutane and neopentane in the gas phase.

Another way of preparing the $[Ta]_s$—H tantalum hydride catalyst is as follows:

the silica is dehydroxylated beforehand at a temperature greater than 500° C. (up to 1100° C.), so as to bring about the appearance at the surface of more or less strained siloxane bridges resulting from the condensation of the hydroxyl groups; tris(neopentyl) neopentylidenetantalum $Ta[-CH_2-CMe_3]_3[=CH-CMe_3]$ is sublimed at 80° C. and reacts both with the remaining hydroxyl groups and with the siloxane bridges according to:

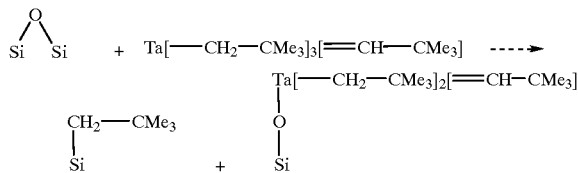

Conversion of the neopentyl-neopentylidene complexes to the surface tantalum hydrides takes place as above by treatment under hydrogen.

EXAMPLE 2
Preparation of the Tungsten Hydride Catalyst

The $[W]_s$—H surface tungsten hydride catalyst can be prepared in the following way: tris(neopentyl) neopentylidynetungsten $W[-CH_2-CMe_3]_3[\equiv C-CMe_3]$ is sublimed at 80° C. in a glass reactor over silica dehydroxylated beforehand at 500° C., so as to graft the tungsten complex by a reaction at 25° C. with one or more hydroxyl groups of the silica surface. The mixture of the tungsten complexes which are obtained is subsequently treated under hydrogen at atmospheric pressure at 150° C. for 15 h, so as to form the supported hydride species; this reaction is accompanied by the hydrogenolysis of the neopentyl and neopentylidene ligands, producing methane, ethane, propane, isobutane and neopentane in the gas phase.

EXAMPLE 3
Reaction for the Metathesis of Ethane:

The $[Ta]_s$—H tantalum hydride catalyst supported on silica (52.2 mg; 4.89% $Ta/SiO_2$; 14.1 micromol of Ta) is prepared in situ in a glass reactor as described above. The reactor is placed under vacuum, then filled with ethane at atmospheric pressure (ethane/Ta=800) and heated at 150° C. under batch conditions; the formation mainly of methane and of propane, as well as of butane and of isobutane, is then observed according to Table I:

TABLE I

Reaction for the metathesis of ethane at 150° C. (ethane/Ta = 800).

| | | Number of moles of hydrocarbons formed per mole of surface tantalum | | | |
|---|---|---|---|---|---|
| Time (h) | Rotations[a] | $CH_4$ | $C_3H_8$ | isobutane | n-butane |
| 2.5 | 3.1 | 1.59 | 1.43 | 0.02 | 0.07 |
| 22 | 12.2 | 8.13 | 5.13 | 0.09 | 0.11 |
| 82 | 46.4 | 26.54 | 20.28 | 0.63 | 0.73 |

[a]number of moles of ethane converted with respect to the tantalum

EXAMPLE 4
Reaction for the Metathesis of Propane:

The $[Ta]_s$—H catalyst (46.6 mg; 4.44% Ta/SiO$_2$; 11.4 micromol of Ta) is prepared as in Example 3 and then the reactor charged with propane at atmospheric pressure (propane/Ta=880) and heated at 150° C. under batch conditions. A mixture of methane, of ethane, of butane, of isobutane and, in a smaller proportion, of pentane, of isopentane and of C$_6$ homologues is gradually obtained according to the following Table 2.

EXAMPLE 5
Reaction for the Metathesis of Butane:

The $[Ta]_s$—H catalyst (53.3 mg; 4.78% Ta/SiO$_2$; 14.1 micromol of Ta) is prepared as in Example 3 and then the reactor is charged with butane at atmospheric pressure (butane/Ta=900) and heated at 150° C. under batch conditions. A mixture of ethane, of propane, of pentane and, in smaller proportions, of methane, of isobutane, of isopentane and of C$_6$ homologues is gradually obtained according to the following Table 3.

EXAMPLE 6
Reaction for the Metathesis of Isobutane:

The $[Ta]_s$—H catalyst (66 mg; 9.52% Ta/SiO$_2$; 34.7 micromol of Ta) is prepared as in Example 3 and then the reactor is charged with isobutane at atmospheric pressure (isobutane/Ta=244) and heated at 150° C. under batch conditions. A mixture of methane, of ethane, of propane, of neopentane, of isopentane and of 2-methylpentane and, in smaller proportions, of n-butane and of 2-methylhexane is gradually obtained according to the following Table 4.

EXAMPLE 7
Reaction for the Metathesis of Propane at 150° C. over $[W]_s$—H/SiO$_2$ Catalyst:

The $[W]_s$—H catalyst (55.7 mg; 4.96% W/SiO$_2$; 15.01 micromol of W) supported on silica is prepared as described above and then the reactor is charged with propane at atmospheric pressure (propane/W=790) and heated at 150° C. under batch conditions. A mixture of methane, of ethane, of isobutane, of butane, of pentane and, in a smaller proportion, of isopentane and of hexane is gradually obtained according to the following Table 5.

TABLE 2

Reaction for the metathesis of propane at 150° C. (propane/Ta = 880)

| | | Number of moles of hydrocarbons formed per mole of surface tantalum | | | | | | | | |
|---|---|---|---|---|---|---|---|---|---|---|
| Time (h) | Rotations | CH$_4$ | C$_2$H$_6$ | ibt[a] | nbut[b] | 2mbt[c] | npent[d] | C6[e] | C6[e] | nhex[f] |
| 5 | 14 | 3.32 | 5.95 | 1.05 | 4.34 | 0.34 | 0.70 | | | |
| 20 | 36.3 | 8.58 | 15.83 | 3.03 | 10.72 | 0.94 | 1.77 | | | |
| 43 | 43.8 | 9.39 | 18.07 | 3.58 | 12.91 | 1.13 | 2.22 | 0.11 | 0.09 | 0.32 |

[a]i-butane, [b]n-butane, [c]2-methylbutane, [d]n-pentane, [e]isomers of n-hexane, [f]n-hexane.

TABLE 3

Reaction for the metathesis of butane at 150° C. (butane/Ta = 900)

| | | Number of moles of hydrocarbons formed per mole of surface tantalum | | | | | | | | |
|---|---|---|---|---|---|---|---|---|---|---|
| Time (h) | Rotations | CH$_4$ | C$_2$H$_6$ | C$_3$H$_3$ | ibt[a] | 2mbt[c] | npent[d] | C6[d] | C6[d] | nhex[e] |
| 1.25 | 7 | 0.58 | 1.06 | 3.83 | 1.4 | 0.24 | 1.30 | | | |
| 7.25 | 23.6 | 2.07 | 4.00 | 14.76 | 2.21 | 0.95 | 5.34 | | | |
| 23.25 | 40 | 2.38 | 6.24 | 22.71 | 2.55 | 1.15 | 7.86 | 0.32 | 1.16 | 3.13 |
| 138.25 | 66.5 | 2.78 | 10.66 | 36.33 | 3.00 | 1.97 | 14.29 | 0.58 | 0.32 | 5.72 |

[a]i-butane, [b]2-methylbutane, [c]n-pentane, [d]isomers of n-hexane, [e]n-hexane.

TABLE 4

Reaction for the metathesis of isobutane at 150° C. (isobutane/Ta = 244)

| | | Number of moles of hydrocarbons formed per mole of surface tantalum | | | | | | | |
|---|---|---|---|---|---|---|---|---|---|
| Time (h) | Rotations | CH$_4$ | C$_2$H$_6$ | C$_3$H$_8$ | n-C$_4$[a] | NpH[b] | i-C$_5$[c] | i-C$_6$[d] | i-C$_7$[e] |
| 3 | 3.3 | 1.38 | 0.87 | 1.33 | 0.15 | 0.3 | 0.44 | 0.27 | 0.04 |
| 23 | 9.5 | 2.23 | 3.28 | 2.38 | 0.08 | 0.4 | 1.79 | 1.53 | 0.23 |
| 47 | 11.5 | 2.71 | 4.96 | 2.95 | 0.09 | 0.65 | 2.02 | 1.62 | 0.15 |

[a]n-butane, [b]neopentane, [c]isopentane, [d]2-methylpentane, [e]2-methylhexane.

TABLE 5

Reaction for the metathesis of propane at 150° C. over [W]$_s$-H/SiO$_2$ catalyst (propane/W = 790)

| Time (h) | Rotations | CH$_4$ | C$_2$H$_6$ | ibt[a] | nbut[b] | 2mbt[c] | npent[d] | nhex[e] |
|---|---|---|---|---|---|---|---|---|
| 2 | 3.4 | 0.09 | 2.04 | 0.06 | 1.25 | | 0.14 | |
| 4 | 6.7 | 0.12 | 4.16 | 0.11 | 2.42 | | 0.33 | |
| 20 | 11.7 | 0.24 | 7.49 | 0.25 | 3.9 | 0.07 | 0.62 | 0.09 |

Number of moles of hydrocarbons formed per mole of surface tantalum

[a]i-butane, [b]n-butane, [c]2-methylbutane, [d]n-pentane, [e]n-hexane.

What is claimed is:

1. Process for metathesis of linear or branched starting alkanes comprising
   reacting the linear or branched starting alkanes over a solid catalyst under the metathesis condition said alkanes, the solid catalyst comprising a solid oxide grafted with metal atoms in the form of hydrides dispersed over the solid oxide.
2. Process according to claim 1, characterized in that the metal atoms of the solid catalyst in the form of hydrides exhibit high degrees of unsaturation.
3. Process according to claim 1, characterized in that the solid catalyst is obtained from:
   a) an organometallic complex of formula (II)

$$MR_a \qquad (II)$$

where
   M is a transition metal selected from those of groups 5 and 6 of the Periodic Classification of the Elements,
   the R groups are identical or different, saturated or unsaturated, hydrocarbon-comprising ligands bonded to the M by one or more carbons, and
   a is less than or equal to the valency of M, which is 5 or 6; and
   b) an anhydrous solid oxide.
4. Process according to claim 3, characterized in that the hydrocarbon-comprising ligands are C$_1$ to C$_{10}$ hydrocarbon-comprising ligands.
5. Process according to claim 3, characterized in that the anhydrous solid oxide is obtained by heat treating the solid oxide to dehydrate and dehydroxylate the solid oxide.
6. Process according to claim 3, characterized in that the solid catalyst is obtained by
   sublimation of the organometallic complex, followed by
   grafting the organometallic complex to the solid oxide, followed by
   hydrogenolysis of the carbon-comprising ligand to convert the metal to hydride.
7. Process according to claim 6, characterized in that the temperature of the sublimation step is about 80° C.
8. Process according to claim 6, characterized in that the sublimation is carried out under vacuum at a temperature between 50 and 15° C.
9. Process according to claim 6, characterized in that the grafting reaction is carried out at a temperature greater than or equal to ambient temperature.
10. Process according to claim 6, characterized in that, instead of a sublimation, the dispersion and the grafting are carried out starting with a solution of the organometallic complex in an organic solvent and by bringing this solution into contact with the solid oxide.
11. Process according to claim 6, characterized in that the hydrogenolysis is carried out in the presence of hydrogen under a pressure of between 10$^{-2}$ and 100 bar, at a temperature of between 25 and 400° C., and for a period of time ranging from 1 h to 24 h.
12. Process according to claim 11, characterized in that the pressure of the hydrogenolysis is atmospheric pressure.
13. Process according to claim 12, characterized in that the temperature of the hydrogenolysis is about 150° C.
14. Process according to claim 13, characterized in that the pressure of the hydrogenolysis is atmospheric pressure.
15. Process according to claim 1, characterized in that the metal atoms are selected from the group consisting of tantalum, tungsten, and chromium.
16. Process according to claim 1, characterized in that the solid oxide is selected from the group consisting of silica, alumina, silica-alumina, niobium, oxide, and zeolites.
17. Process according to claim 16, characterized in that the solid catalyst is a tantalum, tungsten, or chromium hydride grafted to silica or silica-alumina.
18. Process according to claim 1, characterized in that the metathesis reaction is carried out at a temperature of between 25 and 300° C.
19. Process according to claim 18, characterized in that the temperature is between 100 and 200° C.
20. Process according to claim 1, characterized in that the metathesis reaction is carried out by passing the alkane or alkanes in the gas phase over the solid catalyst.
21. Process according to claim 20, characterized in that the metathesis reaction is carried out by passing the alkane or alkanes in the gas phase at a pressure greater than or equal to atmospheric pressure but less than or equal to the condensation pressure of the alkane or of the heaviest alkane when there are several starting alkanes.
22. Process according to claim 1, characterized in that the reaction is carried out under a pressure of between 10$^{-2}$ and 100 bar.
23. Process according to claim 22, characterized in that the reaction is carried out starting from atmospheric pressure.
24. Process according to claim 1, characterized in that the metathesis reaction is carried out with the solid catalyst in suspension in a liquid phase of the alkane or alkanes.
25. Process according to claim 1, characterized in that the metathesis reaction is carried out in the presence of at least one inert gas.
26. Process according to claim 25, characterized in that the inert gas is selected from the group consisting of nitrogen, helium, and argon.
27. Process according to claim 1, characterized in that the starting alkane or alkanes is/are selected from the group consisting of linear C$_2$–C$_{30}$ alkanes, branched C$_4$–C$_{30}$ alkanes, and cyclic hydrocarbons substituted by at least one linear or branched alkane chain.
28. Process according to claim 27, characterized in that the cyclic hydrocarbons are aromatic rings or saturated rings.
29. Process according to claim 27, characterized in that the hydrocarbon is a substituted saturated ring according to the formula (III)

$$(CH_2)_x\!-\!CH\!-\!(CH_2)_y\!-\!CH_3 \qquad (III)$$

where
x is greater than or equal to 2 and
y is greater than or equal to 0.

30. Process according to claim 29, characterized in that x is between 2 and 20.

31. Process according to claim 29, characterized in that y is between 0 and 29.

32. Process according to claim 31, characterized in that x is between 2 and 20.

33. Process according to claim 27, characterized in that the alkane or alkanes is/are selected from the group consisting of ethane, propane, butane, pentane, isobutane, isopentane, 2-methylpentane, 3-methylpentane and 2,3-dimethybutane.

34. Process according to claim 1, characterized in that at least two alkanes selected from linear or branched alkanes and cyclic hydrocarbons substituted by at least one linear or branched chain are reacted together.

\* \* \* \* \*

UNITED STATES PATENT AND TRADEMARK OFFICE
CERTIFICATE OF CORRECTION

PATENT NO. : 6,229,060 B1
APPLICATION NO. : 09/147507
DATED : May 8, 2001
INVENTOR(S) : Vidal et al.

Page 1 of 1

It is certified that error appears in the above-identified patent and that said Letters Patent is hereby corrected as shown below:

Col. 9 Line 16 Claim 1: Add "of" between "metathesis condition" and "said alkanes"

Col. 9 Line 55 Claim 8: change 15° C to 150° C

Signed and Sealed this

First Day of September, 2009

David J. Kappos
*Director of the United States Patent and Trademark Office*